(12) United States Patent
Chang et al.

(10) Patent No.: US 11,446,259 B2
(45) Date of Patent: Sep. 20, 2022

(54) CURCUMINOID COMPOSITIONS AND PREPARATION METHODS

(71) Applicant: InovoBiologic Inc., Calgary (CA)

(72) Inventors: Chuck Chang, Burnaby (CA); Sangho Lee, Burnaby (CA); Youngse Jang, Burnaby (CA); Yoon Seok Roh, Burnaby (CA)

(73) Assignee: InovoBiologic Inc., Calgary (CA)

( * ) Notice: Subject to any disclaimer, the term of this patent is extended or adjusted under 35 U.S.C. 154(b) by 0 days.

(21) Appl. No.: 16/143,194

(22) Filed: Sep. 26, 2018

(65) Prior Publication Data

US 2019/0105286 A1 Apr. 11, 2019

Related U.S. Application Data

(60) Provisional application No. 62/564,837, filed on Sep. 28, 2017.

(51) Int. Cl.
| | | |
|---|---|---|
| *A61K 31/12* | (2006.01) | |
| *A61K 9/14* | (2006.01) | |
| *A61K 9/48* | (2006.01) | |

(52) U.S. Cl.
CPC .............. *A61K 31/12* (2013.01); *A61K 9/141* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | |
|---|---|---|
| 7,883,728 B2 | 2/2011 | Antony |
| 8,187,615 B2 | 5/2012 | Friedman |
| 8,551,507 B2 | 10/2013 | Liu |
| 2002/0102280 A1* | 8/2002 | Anderson ............ A61K 9/1075 |
| | | 424/400 |
| 2010/0316631 A1 | 12/2010 | Safavy |
| 2011/0033525 A1 | 2/2011 | Liu |
| 2013/0274343 A1 | 10/2013 | Deshpande et al. |
| 2017/0304204 A1* | 10/2017 | Fahrner .................. A61K 9/146 |

FOREIGN PATENT DOCUMENTS

| | | |
|---|---|---|
| WO | 2012024405 | 2/2012 |
| WO | 2013175507 | 11/2013 |
| WO | 2014025672 | 2/2014 |
| WO | 2014068597 | 5/2014 |
| WO | 2015025263 | 2/2015 |

* cited by examiner

*Primary Examiner* — Patricia Duffy
*Assistant Examiner* — Garen Gotfredson
(74) *Attorney, Agent, or Firm* — Christensen O'Connor Johnson Kindness PLLC (57) ABSTRACT

Provided herein are water soluble solid form compositions including a curcuminoid; and a solubilizer selected from one or more of methylsulfonylmethane (MSM) and steviol glycoside; glycerol polyethylene glycol hydroxystearate (GPGH) and steviol glycoside; fatty acid glycerol polyglycoester (GPE); steviol glycoside and an aromatic amino acid; and steviol glycoside. Also provided herein are methods of making the water soluble solid form compositions.

6 Claims, 6 Drawing Sheets

CURCUMINOID COMPOSITIONS AND PREPARATION METHODS

TECHNICAL FIELD

This invention relates to the field of curcuminoids. In particular, the invention relates to solid form water soluble curcuminoid compositions and methods of preparing same.

BACKGROUND

Curcumin is the major curcuminoid of the Indian curry spice turmeric. Curcuminoids provide the major yellow color pigment of turmeric, which is derived from the rhizome of the *Curcuma longa linn* plant and it has been traditionally used in the treatment of skin wounds, inflammation, tumors et al.

Although raw turmeric contains more than 100 components, its characteristic yellow color is derived from various curcuminoids. Curcuminoids have a chemical structure consisting of 2 aromatic rings joined by a 7-carbon chain with various substituents.

Curcumin (1,7bis (4-hydroxy-3-methoxy phenyl)-1,6 heptadiene-3,5-dione) is a hydrophobic polyphenol derivative which is a potent antioxidant derived from the spice turmeric. Commercial "curcumin" is a mixture of diarylheptanoid compounds, that usually a combination of about 77% diferuloylmethane (i.e. curcumin), 17% demethoxycurcumin, and 6% of bisdemethoxycurcumin.

Curcuminoids are the primary active ingredients of *Cucuma longa* rhizome (the turmeric plant). These curcuminoids are often identified as curcumin 1 (diferuylmethane), curcumin 2 (demethoxycurcumin), curcumin 3 (didemethoxycurcumin) and cyclocurcumin (A. Goel and A. B. Kunnumakkara, 2008). Curcumin 1 (diferuylmethane) is the most potent of the naturally occurring curcuminoids.

Curcuminoids are natural phenolic compounds that are responsible for the yellow color of turmeric. Curcumin exists in several tautomeric forms.

Curcuminoids are generally hydrophobic compounds thought to have a variety of therapeutic benefits (for example, anti-inflammatory, anti-oxidant, anti-cancerous activities). However, their therapeutic use has been limited by their hydrophobicity which results in poor solubility and rapid elimination from the body (i.e. low bioavailability).

While the poor bioavailability of curcumin is attributable to its poor absorption in the body, it is also quickly metabolized and rapidly eliminated from the body.

Curcuminoids have been shown to have potent activity against pancreatic cancer, to inhibit gastrointestinal carcinogenesis, and to protect against oxidative stress. It is also reported to have chemopreventative, chemotherapeutic, chemosensitizing, and radio-protective in normal cells and radiosensitizing in cancer cells. Curcumin has been reported to exhibit anti-tumor and anti-apoptotic properties and to suppress the growth of a variety of cancer cell lines in the laboratory and prevent the appearance of cancers in animal studies (Araujo and Leon, 2001).

In order to overcome the poor bioavailability of curcuminoid compounds, various efforts have been made to increase their bioavailability through complexing with cyclodextrins, micelles and nanoparticles.

Curcumin has chemo preventive, anti-neoplastic and anti-inflammatory properties in preclinical animal models (Gary J. Kelloff New Agents for Cancer Chemoprevention *Journal of Cell Biochemistry* (1996) 63 Supplement S26:1-28).

S. K Kulkarni demonstrate a role for curcumin in enhancing neurogenesis, notably in the frontal cortex and hippocampal regions of the brain ("Potentials of Curcumin as an Antidepressant" *Scientific World Journal* (2009) 9:1233-1241).

The synthesis and physiochemical characterization of a polymer based nanoparticle of curcumin called 'nanocurcumin' with less than 100 nm particle size was described by Savita Bisht et al. ("Polymeric nanoparticle-encapsulated curcumin ("nanocurcumin"): a novel strategy for human cancer therapy Journal of Nanobiotechnology (2007)5:3). The nanocurcumin was found to have similar in vitro activity as that of free curcumin in pancreatic cell lines.

WO2013175507 titled "Novel highly bioavailable, water soluble and sustained release nano-formulations of hydrophobic plant derived compounds and extracts" describes a nano-emulsified composition to enhance bioavailability of curcuminoids. The concentration of the emulsifier phase in the nanoformulations ranges from 60% to 95%. In addition, the application describes the use of emulsifiers which are anionic, cationic or non-ionic selected from but not limited to Polysorbates preferably Polysorbate 80 and Polysorbate 20, Polyethylene glycols preferably Polyethylene glycol 200 and Polyethylene glycol 400, Polyethylene glycol esters and Glycerol esters and also tabulates a series of composition of nanoformulations using hydrophobic compounds and also disclosed a process of pre-heating the emulsifier phase to a temperature below the melting point of the hydrophobic active ingredient. Analytical results for the particle size of CurQlife (curcumin), morphological characteristics of CurQlife are provided, along with an aqueous phase curcumin concentration ranging from 5 to 20%. Furthermore, the maximum curcumin concentration achieved in human pharmacokinetic study was about 25 ng/mL.

U.S. Pat. No. 7,883,728 titled "Composition to enhance the bioavailability of curcumin" provides a method to improve bioavailability of curcumin preparation of a composition containing purified curcuminoid and purified oil and discloses a methodology to prepare a composition for enhanced bioavailability. The composition comprises a curcuminoid mixture consisting of demethoxycurcumin and bisdemethoxycurcumin and the essential oil arturmerone. The percent ratios of the composition consist of a range of 24% to 96% of curcuminoids combined with a range of 4% to 50% of the essential oil. The bioavailability of curcumin in human was shown to reach a maximum of about 93 ng/g.

WO2012024405 titled "Curcumin compositions and uses thereof" describes a composition and a method of increasing the bioavailability of curcumin. The composition is suitable for modifying DNA methylation and for treatment of cancer. The composition comprises curcumin and excipient polymers like polyethoxylated castor oil, polyoxyethylenesorbitan ester and polyethylene glycol. The application described the increased bioavailability of curcumin by using gel formulation and the formulation is safe, tolerated and effective in treatment of leukemia and breast cancer. The plasma level of curcumin was high in human volunteers thus increasing the bioavailability of curcumin. However, the invention is silent with respect to the absorption of curcumin from blood and its dispersibility, which affects the bioavailability.

WO2014068597, titled "Formulation of curcumin with enhanced bioavailability of curcumin and method of preparation and treatment thereof", provides a medicinal composition useful for the treatment of head and neck cancer premalignant lesions comprising (a) curcuminoid mixture and (b) an essential oil of turmeric. The weight ratios of curcuminoid mixtures to turmeric essential oil ranging from about 1:3 to about 99:1. Also disclosed, is a method of treating head and neck oral premalignant lesion by the administration of medicinal composition comprising curcuminoid mixture and added essential oil of turmeric to patients suffering from such disease.

WO2015025263 titled "A novel composition of curcumin with enhanced bioavailability", discloses a curcumin composition for increasing the bioavailability of curcumin, which consists of curcumin mixture and a water extract of turmeric in a ratio of 70:30, wherein the curcumin mixture comprises curcumin dry crystals, volatile oil, fixed oil and the water extract comprises soluble proteins, dietary fibers and carbohydrates extracted from turmeric, and the composition also consists of a natural emulsifier isolated from *Quillaja saponaria* and lecithin and a method of preparing the composition.

US patent publication US2010/0316631 titled "Water Soluble Curcumin-based Compositions" discloses the design and synthesis of water soluble curcumin-based compositions, methods for synthesizing the compositions and methods of treatment using the compositions.

US patent publication US2013/0274343 titled "Water Soluble Composition comprising Curcumin having enhanced bioavailability and process thereof" describes a water soluble composition having enhanced bioavailability and a process for its preparation.

U.S. Pat. No. 8,551,507, titled "Terpene glycosides and their combinations as solubilizing agents" discloses methods and compositions for enhancing solubility of organic compounds including curcuminoids with terpene glycosides, wherein combinations include curcuminoids with 1% to 40% w/v mogroside V and curcuminoids with 1% to 40% w/v geniposide. Stevioside was shown to enhance the solubility of clofazinine, digoxin, oleandrin, nifedipine, and amiodarone, but does not appear to have been combined with curcumin.

US patent publication US2011/0033525, titled "Diterpene Glycosides as Natural Solubilizers" discloses methods for enhancing curcuminoid solubility by mixing it with water and a diterpene glycoside such as rubusoside, rebaudioside, steviol monoside and stevioside. Rubusoside was used to increase the solubility of curcumin in water by a factor of 285 and another example discloses that 5% stevioside in water was equally effective to rubusoside in solubilizing curcumin. All of the compositions disclosed as enhancing solubility were aqueous solutions and no solid form composition was disclosed.

PCT/US2013/053585 describes water soluble compositions of curcumin were formulated containing macrogolglycerol hydroxystearate (polyoxyl 40 castor oil) and curcumin extract that is 99% pure, 1,7-Bis(4-hydroxy-3-methoxyphenyl)-1,6-heptadiene-3,5-dione by HPLC, wherein the polyoxyl 40 castor oil (non-ionic surfactant) was heated and stirred to a temperature of about 125° F. (about 52° C.), and the curcumin powder was slowly mixed with the polyoxyl castor oil until a clear viscous solution was formed containing dissolved curcumin powder. The curcumin emulsion was then slowly added to warm water (100-125° F.) until a crystal clear solution was formed.

U.S. Pat. No. 8,187,615 discloses non-aqueous compositions for oral delivery of insoluble bioactive agents (for example, curcumin) wherein polyethylene glycol is one of the pharmaceutically acceptable water-miscible non-aqueous solvents.

SUMMARY

The present invention is based, in part, on the discovery that curcuminoids are made more water soluble and thus more bioavailable to a subject when combined with a solubilization matrix as described herein.

In one aspect, there is provided a method of producing a solid form water soluble curcuminoid composition, the method including: (a) mixing a curcuminoid and a solubilization matrix to form a mixture; (b) adjusting the temperature of the mixture to between about 60° C. and about 190° C. to dissolve the curcuminoid; and (c) cooling the mixture to permit the curcuminoid and the solubilization matrix composition to achieve a solid form; wherein the solubilization matrix may be selected from one or more of the following: (i) methylsulfonylmethane (MSM) and steviol glycoside; (ii) glycerol polyethylene glycol hydroxystearate (GPGH) and steviol glycoside; (iii) fatty acid glycerol polyglycoester (GPE) and steviol glycoside; (iv) steviol glycoside and an aromatic amino acid; and (v) steviol glycoside. Alternatively, the solubilization matrix may be selected from one or more of the following: (i) methylsulfonylmethane (MSM) and steviol glycoside; (ii) glycerol polyethylene glycol hydroxystearate (GPGH) and steviol glycoside; (iii) fatty acid glycerol polyglycoester (GPE) and steviol glycoside; (iv) steviol glycoside and an aromatic amino acid; (v) steviol glycoside; (vi) polyethylene glycol; (vii) glycerol ethoxylate; (viii) steviol glycoside and polyethylene glycol; and (ix) steviol glycoside and glycerol ethoxylate.

The mixture may further include an organic solvent. The organic solvent may be selected from: methanol; ethanol; propanol; butanol; acetonitrile; and acetone. The organic solvent may be added (A) before adjusting the temperature of the mixture in (b); (B) during the adjusting the temperature of the mixture in (b); or (C) the curcumin is dissolved in the organic solvent before mixing with the solubilization matrix. The temperature of the mixture may be kept between about 60° C. and about 90° C. for 20 to 200 minutes to facilitate organic solvent evaporation. The temperature of the mixture may be kept between about 70° C. and about 90° C. for 20 to 200 minutes to facilitate organic solvent evaporation. The temperature of the mixture may be kept between about 80° C. and about 90° C. for 20 to 200 minutes to facilitate organic solvent evaporation. The temperature of the mixture may be kept between about 60° C. and about 90° C. for 40 to 200 minutes to facilitate organic solvent evaporation. The temperature of the mixture may be kept between about 60° C. and about 90° C. for 50 to 200 minutes to facilitate organic solvent evaporation. The temperature of the mixture may be kept between about 60° C. and about 90° C. for 60 to 200 minutes to facilitate organic solvent evaporation. The temperature of the mixture may be kept between about 60° C. and about 90° C. for 70 to 200 minutes to facilitate organic solvent evaporation. The temperature of the mixture may be kept between about 60° C. and about 90° C. for 80 to 200 minutes to facilitate organic solvent evaporation. The temperature of the mixture may be kept between about 60° C. and about 90° C. for 90 to 200 minutes to facilitate organic solvent evaporation. The temperature of the mixture may be kept between about 60° C. and about 90° C. for 10 to 120 minutes to facilitate organic solvent evaporation.

The solid form water soluble curcuminoid composition may be isolated. The aromatic amino acids may be tyrosine, tryptophan, or phenylalanine. The curcuminoid component of the solid form water soluble curcuminoid composition, may be between about 5% and about 70% by weight. The curcuminoid component of the solid form water soluble curcuminoid composition, may be between about 10% and about 60% by weight. The curcuminoid component of the solid form water soluble curcuminoid composition, may be between about 10% and about 50% by weight. The curcuminoid component of the solid form water soluble curcuminoid composition, may be between about 10% and about 40% by weight. The curcuminoid component of the solid form water soluble curcuminoid composition, may be between about 10% and about 30% by weight. The curcuminoid component of the solid form water soluble curcuminoid composition, may be between about 10% and about 20% by weight.

The solubilization matrix component of the solid form water soluble curcuminoid composition, may be between about 30% and about 95% by weight. The solubilization matrix component of the solid form water soluble curcuminoid composition, may be between about 40% and about 80% by weight. The solubilization matrix component of the solid form water soluble curcuminoid composition, may be between about 40% and about 70% by weight. The solubilization matrix component of the solid form water soluble curcuminoid composition, may be between about 40% and about 60% by weight. The solubilization matrix component of the solid form water soluble curcuminoid composition, may be between about 50% and about 70% by weight. The solubilization matrix components may be MSM and steviol glycoside and the MSM and steviol glycoside may be between about 10% and about 90% by weight. The solubilization matrix components may be MSM and steviol glycoside and the MSM and steviol glycoside may be between about 40% and about 80% by weight. The solubilization matrix component may be a steviol glycoside and the steviol glycoside may be between about 5% and about 90% by weight. The solubilization matrix component may be a steviol glycoside and the steviol glycoside may be between about 20% and about 90% by weight. The solubilization matrix component may be a steviol glycoside and the steviol glycoside may be between about 40% and about 80% by weight. The solubilization matrix components may be GPGH and steviol glycoside and the GPGH and steviol glycoside may be between about 30% and about 95% by weight. The solubilization matrix components may be GPGH and steviol glycoside and the GPGH and steviol glycoside may be between about 40% and about 50% by weight. The solubilization matrix components may be GPGH and steviol glycoside and the GPGH and steviol glycoside may be between about 30% and about 95% by weight. The solubilization matrix components may be GPE and steviol glycoside and the GPE and steviol glycoside may be between about 30% and about 80% by weight. The solubilization matrix components may be GPE and steviol glycoside and the GPE and steviol glycoside may be between about 30% and about 70% by weight. The solubilization matrix components may be an aromatic amino acid and steviol glycoside and the aromatic amino acid and steviol glycoside may be between about 10% and about 95% by weight. The solubilization matrix components may be an aromatic amino acid and steviol glycoside and the aromatic amino acid and steviol glycoside may be between about 40% and about 80% by weight.

In another embodiment, there is provided a product produced by the methods described herein.

In a further embodiment, there is provided a water soluble solid form composition, the composition including: (a) a curcuminoid; and (b) a solubilizer, wherein the solubilizer is selected from one or more of: (i) methylsulfonylmethane (MSM) and steviol glycoside; (ii) glycerol polyethylene glycol hydroxystearate (GPGH) and steviol glycoside; (iii) fatty acid glycerol polyglycoester (GPE); (iv) steviol glycoside and an aromatic amino acid; and (v) steviol glycoside.

Alternatively, the solubilizer may be selected from one or more of the following: (i) methylsulfonylmethane (MSM) and steviol glycoside; (ii) glycerol polyethylene glycol hydroxystearate (GPGH) and steviol glycoside; (iii) fatty acid glycerol polyglycoester (GPE) and steviol glycoside; (iv) steviol glycoside and an aromatic amino acid; (v) steviol glycoside; (vi) polyethylene glycol; (vii) glycerol ethoxylate; (viii) steviol glycoside and polyethylene glycol; and (ix) steviol glycoside and glycerol ethoxylate. The aromatic amino acid may be tyrosine, tryptophan, or phenylalanine. The curcuminoid component of the solid form water soluble curcuminoid composition may be between about 5% and about 70% by weight.

The curcuminoid component of the solid form water soluble curcuminoid composition, may be between about 10% and about 60% by weight. The curcuminoid component of the solid form water soluble curcuminoid composition, may be between about 10% and about 50% by weight. The curcuminoid component of the solid form water soluble curcuminoid composition, may be between about 10% and about 40% by weight. The curcuminoid component of the solid form water soluble curcuminoid composition, may be between about 10% and about 30% by weight. The curcuminoid component of the solid form water soluble curcuminoid composition, may be between about 10% and about 20% by weight.

The solubilization matrix component of the solid form water soluble curcuminoid composition, may be between about 30% and about 95% by weight. The solubilization matrix component of the solid form water soluble curcuminoid composition, may be between about 40% and about 80% by weight. The solubilization matrix component of the solid form water soluble curcuminoid composition, may be between about 40% and about 70% by weight. The solubilization matrix component of the solid form water soluble curcuminoid composition, may be between about 40% and about 60% by weight. The solubilization matrix component of the solid form water soluble curcuminoid composition, may be between about 50% and about 70% by weight. The solubilization matrix component of the solid form water soluble curcuminoid composition, may be between about 70% and about 90% by weight. The solubilization matrix components may be a MSM and a steviol glycoside, and the MSM and the steviol glycoside may be between about 10% and about 90% by weight. The solubilization matrix components may be a MSM and a steviol glycoside, and the MSM and the steviol glycoside may be between about 40% and about 80% by weight. The solubilization matrix components may be a steviol glycoside and the steviol glycoside may be between about 5% and about 90% by weight. The solubilization matrix components may be a steviol glycoside and the steviol glycoside may be between about 20% and about 90% by weight. The solubilization matrix components may be a steviol glycoside and the steviol glycoside may be between about 40% and about 80% by weight. The solubilization matrix components may be a GPGH and a steviol glycoside, and the GPGH and the steviol glycoside may be between about 30% and about 95% by weight. The solubilization matrix components may be a GPGH and a steviol glycoside, and the GPGH and the steviol glycoside may be between about 40% and about 50% by weight. The solubilization matrix components may be a GPGH and a steviol glycoside, and the GPGH and the steviol glycoside may be between about 30% and about 95% by weight. The solubilization matrix components may be a GPE and a steviol glycoside, and the GPE and the steviol glycoside may be between about 30% and about 80% by weight. The solubilization matrix components may be a GPE and a steviol glycoside, and the GPE and the steviol glycoside may be between about 30% and about 70% by weight. The solubilization matrix components may be an aromatic amino acid and a steviol glycoside, and the aromatic amino acid and the steviol glycoside may be between about 10% and about 95% by weight. The solubilization matrix components may be an aromatic amino acid and a steviol glycoside, and the aromatic amino acid and the steviol glycoside may be between about 40% and about 80% by weight. The solubilization matrix component may be MSM:steviol glycoside in a 7:3 ratio and may be between about 70% and about 90% by weight. The solubilization matrix component may be GPGH:steviol glycoside in a 7:3 ratio and may be between about 70% and about 90% by weight. The solubilization matrix component may be GPGH:steviol glycoside in a 8:2 ratio and may be between about 70% and about 90% by weight. The solubilization matrix component may be tyrosine:steviol glycoside in a 5:5 ratio and may be between about 70% and about 90% by weight.

In a further embodiment, there is provided a method of producing a solid form water soluble curcuminoid composition, the method including: (a) dissolving a curcuminoid in ethanol to produce a curcuminoid solution; (b) steviol glycoside and methylsulfonylmethane (MSM) are mixed and heated in a vacuum chamber to at least about 50° C.; (c) curcuminoid solution is sprayed into the vacuum chamber; and (d) product from step (c) is dried under vacuum.

The curcuminoids may be approx. 95% pure. The dissolving in ethanol may be to about 20% w/w concentration. The method may further include blending of one or more processing aids with the dried product from step (d). The one or more processing aids may be selected from: a cellulose; a mineral compound; a lubricant; a binder; a desiccant; a bulking agent; and a diluent. A cellulose may be a microcrystalline cellulose or a carboxymethyl cellulose. A mineral compound may be a calcium phosphate, a calcium carbonate, or a magnesium oxide. A lubricant may be a stearic acid or a magnesium stearate. A binder may be a guar gum, a carrageen gum, a xanthan gum or a gelatin. A desiccant may be a bentonite clay, a calcium chloride, a calcium oxide or a silica. A diluent may be a rice flour, a wheat flour or a corn flour.

DETAILED DESCRIPTION

Any terms not directly defined herein shall be understood to have the meanings commonly associated with them as understood within the art of the invention.

The term "curcuminoid" as used herein, is meant to encompass a variety of linear diarylheptanoid compounds of natural and synthetic origins or even compounds of natural origin that are subsequently synthetically modified. A diarylheptanoid consists of two aromatic rings (aryl groups) joined by a seven carbons chain (heptane) or seven carbons forming a ring and linear linker (for example, see cyclocurcumin) and allowing for various substituents. Common curcuminoids may include one or more of the following:

dihydrocurcumin-glucuronoside tetrahydrocurcumin-glucuronoside curcuminsulphate hexahydrocurcumin

The Indian spice turmeric, which is derived from the rhizome of the plant *Curcuma longa*, is a natural source of the curcumin. However, curcuminoids are found in many other plant families and the extracted curcuminoids may be modified to form curcuminoids derivatives. The most common curcuminoid derivatives are substituted on the phenyl groups, but may also have variations in the linking chain as shown above.

The term "methylsulfonylmethane" (MSM) as used herein refers to an organosulfur compound with the formula $(CH_3)_2SO_2$. MSM is also known by several other names including $DMSO_2$, methyl sulfone, and dimethyl sulfone. The structure of MSM is The term "solubilization matrix" as used herein is meant to encompass a particular subset of solubilizers, in particular, wherein the solubilization matrix is selected from one or more of the following:
(i) methylsulfonylmethane (MSM); (ii) MSM and steviol glycoside; (iii) glycerol polyethylene glycol hydroxystearate (GPGH), polyethylene glycols, glycerol ethoxylate and steviol glycoside; (iv) fatty acidglycerol polyglycoester (GPE); (v) or combinations of any of (i)-(iv);

The term "steviol glycoside" refers to a group of glycosides of steviol, and the compound steviol is a diterpene compound having the following structure:

wherein the hydroxyl group and carboxyl group of steviol are capable of linking to one or more sugar molecules (for example, glucose or rhamnose). One such steviol glycoside is stevioside, which has the structure:

The steviol glycoside may be selected from one of more of the following: Stevioside; Rebaudioside A (i.e. 19-O-beta-glucopyranosyl-13-O-(beta-glucopyranosyl(1-2)-beta-glucopyranosyl(1-3))-beta-glucopyranosyl-13- xhydroxykaur-16-en-19-oic acid); Rebaudioside B; Rebaudioside C; Rebaudioside D; Rebaudioside E; Dulcoside A; or Rubusoside. Numerous steviol glycosides are isolated from the leaves of the South American plant *Stevia rebaudiana*. However, Rubusoside is found in the Chinese plant *Rubus chingii*. Stevia may include a 90% Stevioside extract complying with FAO Monograph on Stevio Glycosides (http://www.fao.org/fileadmin/user_upload/jecfa_additives/docs/monograph10/additive-442-m10.pdf).

The term "glycerol polyethylene glycol hydroxystearate" or GPGH is a solubilizer is derived from hydrogenated castor oil and ethylene oxide and is a component in solubilizers like Kolliphor® RH 40. GPGH is described herein as useful for solubilizing curcumin.

The term "polyethylene glycol" or PEG as used herein is a polyether compound with numerous applications. PEG is also known as polyethylene oxide (PEO) or polyoxyethylene (POE), depending on its molecular weight. The general structure of PEG is H—(O—CH2-CH2)n-OH.

The term "glycerol ethoxylate" as used herein is an ethoxylated, nonionic ether of glycerine. Glycerol ethoxylate may be represented by $HO(CH_2CH_2O)_n CH[CH_2(OCH_2CH_2)_n OH]_2$ (wherein n=6-7) and has CAS no. 31694-55-0.

The term "fatty-acid glycerol polyglycoester" (GPE) as used herein refers to a group of non-ionic emulsifiers consisting of polyethylene glycols, polyethylene glycol hydroxystearate, glycol polyglycol esters and glycol ethoxylate or combinations thereof.

The terms "solubilizer" as used herein refers to a substance that improves the solubility of a curcuminoid in water.

The term "solubility" as used herein refers to the property of a solid, liquid, or gaseous chemical substance ("solute") to dissolve in a solid, liquid, or gaseous solvent. The solubility of a substance fundamentally depends on the physical and chemical properties of the solute and solvent as well as on temperature, pressure and the pH of the solution.

The term "organic solvent" as used herein is refers to any solvent having at least 1 carbon atom and 1 hydrogen atom, a low molecular weight, lipophilicity, and volatility, and exist in liquid form at room temperature. Organic solvents may further be grouped as aliphatic or aromatic. Organic solvents are useful because they can dissolve oils, fats, resins, rubber, and plastics. An organic solvent may be selected from: methanol; ethanol; propanol; butanol; acetonitrile; and acetone.

The term "solid form" as used herein refers to a solid dosage form. Common solid dosage forms include capsules, tablets, lozenges, pills, troches or powders. A solid is characterized by structural rigidity and resistance to changes of shape or volume. A solid may be reduced in size to a powder. A powder is a dry, bulk solid composed of a large number of very fine particles that may flow freely when shaken or tilted. The manufacture of solid dosage forms most commonly involve ingredients in powder form. As described herein, the term "solid forms" can usually be used interchangeably with "powders".

Solid forms for oral administration may contain pharmaceutically acceptable binders, sweeteners, disintegrating agents, diluents, flavourings, coating agents, preservatives, lubricants and/or time delay agents or any combinations of the foregoing.

Compositions as described herein may be formulated in a single solid dosage form such as in the form of capsules, tablets, lozenges, pills, troches or powders. In some embodiments, the pharmaceutically acceptable carrier may comprise a capsule. The pharmaceutically acceptable carrier may be made from aqueous solutions of gelling agents such as animal protein including gelatin, plant polysaccharides or their derivatives like carrageenans or modified forms of starch and cellulose.

Various alternative embodiments and examples are described herein. These embodiments and examples are illustrative and should not be construed as limiting the scope of the invention.

EXAMPLES

Example 1: Bioavailability of a Curcumin And Glycerol Polyethylene Glycol Hydroxystearate (GPGH) Composition Seven (7) volunteer subjects aged between 25 and 55 years of age were selected as test subjects. Initially, all of volunteers were advised to take a curcumin and glycerol polyethylene glycol hydroxystearate (GPGH) capsule as shown in TABLE 1 below. Blood samples were then collected before ingesting the capsules and then periodically at 1 hr up to 4 hrs. and then at 2 hr intervals for the remaining 4 hrs. until the end of 8 hours (see TABLE 3). After all blood samples were collected, the blood samples were processed as described below.

TABLE 1

| | | | | | |
|---|---|---|---|---|---|
| CURCUMIN AND GLYCEROL POLYETHYLENE GLYCOL HYDROXYSTEARATE (GPGH) | | | | | |
| Ingredient | Final Wt. (%) | Actual Wt. (g) | Final Wt. (g) after evaporating ethanol | | |
| | | | 30 min | 60 min | 90 min |
| Curcumin | 10 | 5 | | | |
| Ethanol | 5 | 4 | | | |
| GPGH | 85 | 42.5 | | | |
| Total | 100 | 51.5 | 110.80 | 110.60 | 110.30 |

The water-soluble curcumin and glycerol polyethylene glycol hydroxystearate (GPGH) capsules were prepared as follows:
(1) curcumin powder was dissolved in the same weight of ethanol, then mixed with GPGH;
(2) dissolving and mixing in (1) was performed at a temperature range of 60° C.-90° C. without excessively evaporating the ethanol; and
(3) once dissolved, increase the temperature of the mixture above the boiling point of ethanol for a period 30-90 minutes to evaporate as much of the ethanol as much as possible.

Example 2: Bioavailability of a Curcumin and Methylsulfonylmethane (MSM) Composition Seven (7) volunteer subjects aged between 25 and 55 years of age were selected as test subjects. Initially, all of volunteers were advised to take a curcumin and MSM/steviol glycoside capsule as shown in TABLE 2 below. Blood samples were then collected before ingesting the capsules and then periodically at 1 hr up to 4 hrs. and then at 2 hr intervals for the remaining 4 hrs. until the end of 8 hours (see TABLE 3). After all blood samples were collected, the blood samples were processed as described below.

TABLE 2

| | | | | | |
|---|---|---|---|---|---|
| CURCUMIN AND METHYLSULFONYLMETHANE (MSM)/STEVIOL GLYCOSIDE | | | | | |
| Ingredient | Final Wt. (%) | Actual Wt. (g) | Final Wt. (g) after evaporating ethanol | | |
| | | | 30 min | 60 min | 90 min |
| Curcumin | 10 | 5 | | | |
| Ethanol | 5 | 4 | | | |
| MSM/Steviol Glycoside | 85 | 42.5 | | | |
| Total | 100 | 51.5 | 110.80 | 110.60 | 110.30 |

The water-soluble curcumin and with MSM and steviol glycoside (i.e. mixture of stevioglycosides that consisting of stevioside, rebaudioside A, B, C, and D based on the mixture naturally occurring in Stevia leaf, purified to about 90% purity and the content of stevioside as a fraction of total steviol glycosides could range from 40-90%) capsules were prepared as follows:
(1) curcumin powder was dissolved in the same weight of ethanol, then mixed with MSM and steviol glycoside;
(2) dissolving and mixing in (i) was performed at a temperature of 80° C.; and
(3) once dissolved, increase the temperature of the mixture above the boiling point of ethanol for a period 30-90 minutes to evaporate as much of the ethanol as much as possible.

Example 3: Comparison with Commercial Products

Figure 2:
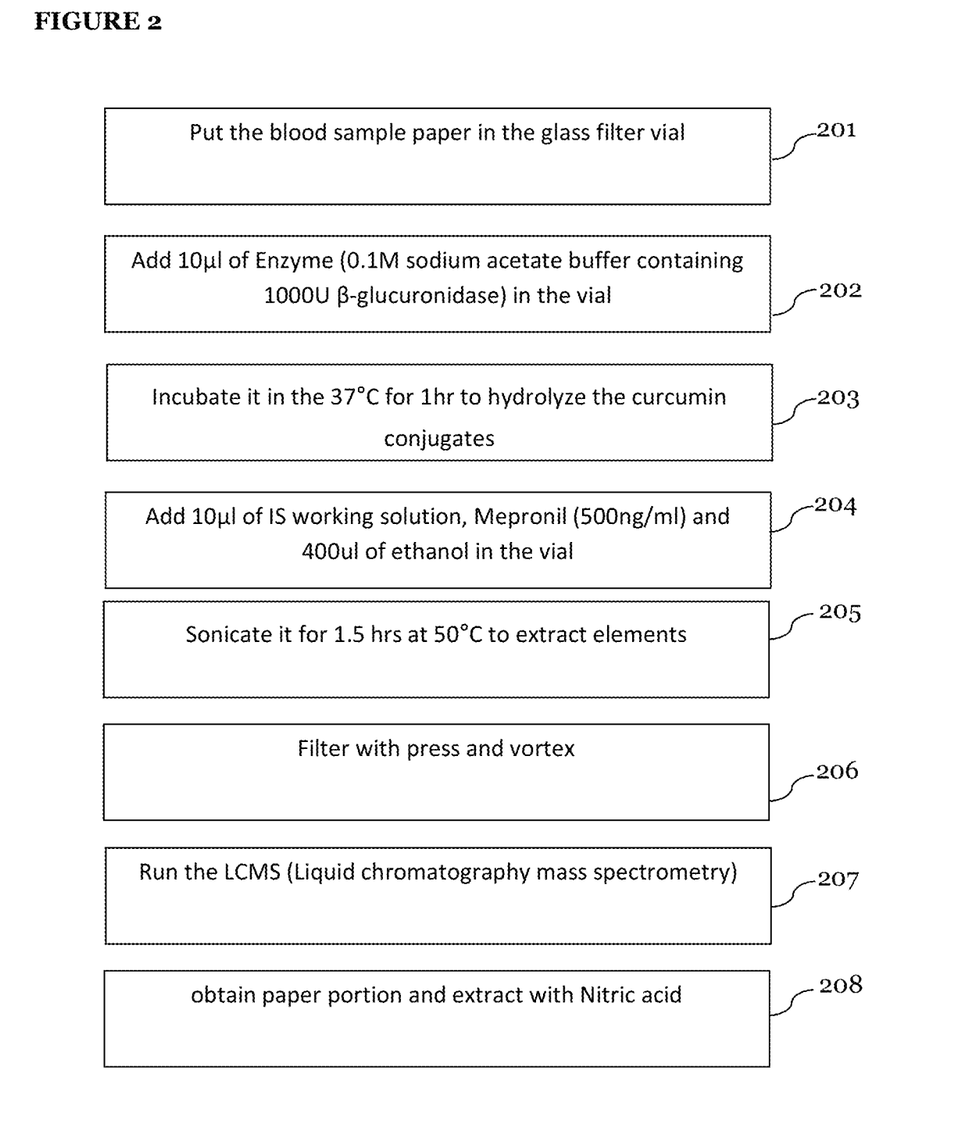
FIG. 2 shows a flow chart of extracting process for blood sample.

Seven (7) volunteer subjects aged between 25 and 55 years of age were selected as test subjects to compare the curcuminoid compositions described in EXAMPLES 1 and 2 above with two commercial curcumin products (Reference #1 and #2—Reference #1 is Theracurmin™ 30%. A commercial product made with micronized curcuminoids and gum ghatti, JP 2009-263638 A; and Reference #2 is Longvide™ Curcumin. A commercial product with lipid micelles of curcuminoids and antioxidants). Blood samples were collected before ingesting commercial curcumin products (Reference #1 and #2) and then periodically at 1 hr up to 4 hrs. and then at 2 hr intervals for the remaining 4 hrs. until the end of 8 hours (see TABLE 3). After all blood samples were collected, the blood samples were processed as described below (see FIG. 2):

(1) put the blood sample paper into the glass filter vial (201), (2) add 100 µl of Enzyme in the vial (202), (3) incubate it in the 37° C. for 1 hour to hydrolyze the curcumin conjugates (203), (4) add 10 µl of an Internal Standard (IS) working solution, Mepronil (500 ng/ml) and 400 µl of Ethanol in the vial (204), (5) sonicate it for 1.5 hours at 50° C. to extract the elements (205), (6) filter with the press and vortex (206), (7) run LCMS (Liquid chromatography mass spectrometry) analysis (207), with an optional nitric acid extraction step (208).

TABLE 3

DATA COLLECTION TIME POINTS FOR TEST SUBJECTS 1-7

| Name | V01 | V02 | V03 | V04 | V05 | V06 | V07 |
|---|---|---|---|---|---|---|---|
| Curcumin(mg) | 180 | 180 | 180 | 180 | 180 | 180 | 180 |
| 0 Hr | V1-0 | V2-0 | V3-0 | V4-0 | V5-0 | V6-0 | V7-0 |
| 1 Hr | V1-1 | V2-1 | V3-1 | V4-1 | V5-1 | V6-1 | V7-1 |
| 2 Hr | V1-2 | V2-2 | V3-2 | V4-2 | V5-2 | V6-2 | V7-2 |
| 3 Hr | V1-3 | V2-3 | V3-3 | V4-3 | V5-3 | V6-3 | V7-3 |
| 4 Hr | V1-4 | V2-4 | V3-4 | V4-4 | V5-4 | V6-4 | V7-4 |
| 6 Hr | V1-6 | V2-6 | V3-6 | V4-6 | V5-6 | V6-6 | V7-6 |
| 8 Hr | V1-8 | V2-8 | V3-8 | V4-8 | V5-8 | V6-8 | V7-8 |

*V01-07 refers to each of the seven (7) volunteer test subjects.

Figure 3A:
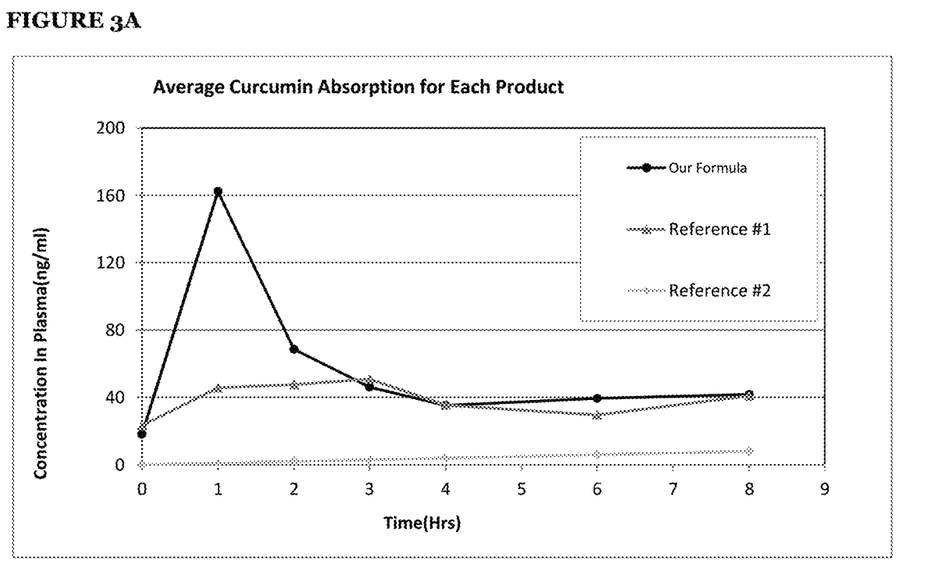
FIGS. 3A and 3B show comparison graphs of curcumin absorption.
Figure 4A:
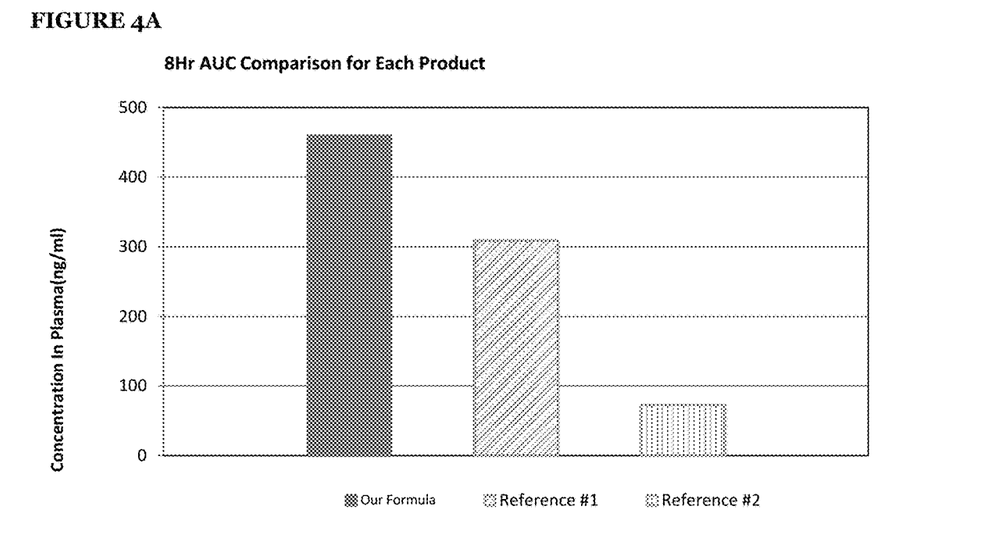
FIGS. 4A and 4B show comparison graphs of total curcumin absorption.

Existing commercial curcumin products (Reference #1 and #2—see FIGS. 3A and 4A) were compared against the curcumin and glycerol polyethylene glycol hydroxystearate (GPGH) composition using the same procedure with a wash out period of at least one week.

Figure 3B:
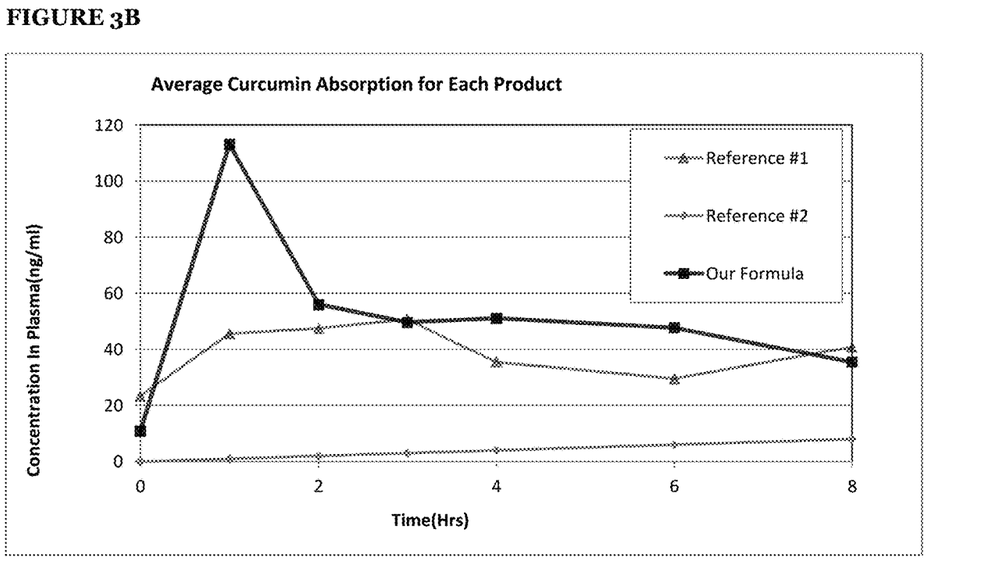
Figure 4B:
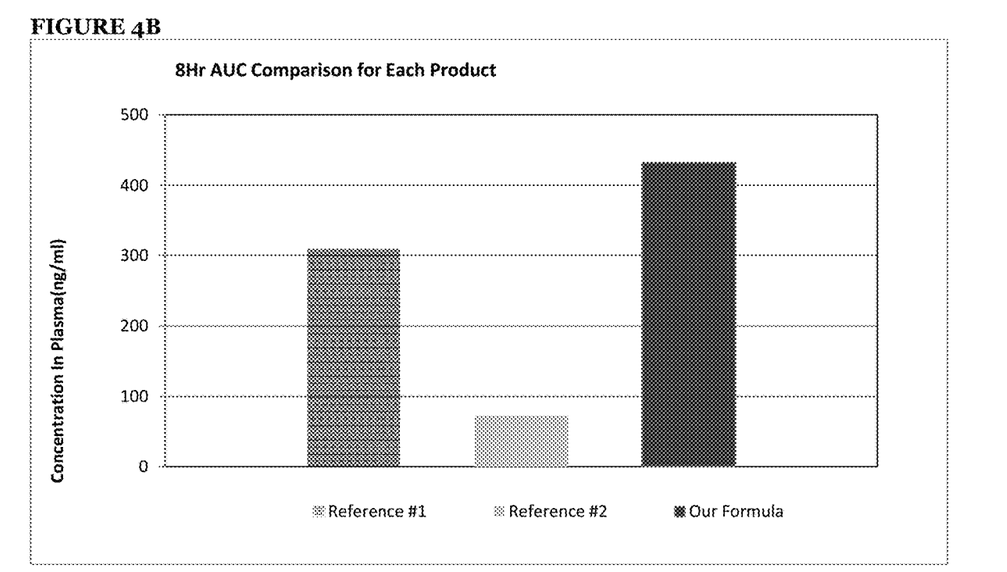

Existing commercial curcumin products (Reference #1 and #2—see FIGS. 3B and 4B) were compared against the curcumin and with MSM and steviol glycoside composition using the same procedure with a wash out period of at least one week.

Example 4: Analysis by High Performance Liquid Chromatography (HPLC)

For this analysis, three different samples were prepared as follows: Reference Sample (Ref) 10% curcuminoid in GPGH; 7:3 Ratio (GPGH & curcuminoid ratio 7:3); and 8:2 Ratio (GPGH & curcuminoid ratio 8:2 to demonstrate an optimal GPGH-to-curcuminoid ratio that provides exceptional water solubility of curcuminoids. HPLC analysis proceeded once the samples were prepared.

As shown in TABLE 4 below, the use of steviol glycosides increases the amount of curcumin component. There were three curminoid compounds in curcumin tested (i.e. BisdemethoxyCurcumin, DemethoxyCurcumin, and Curcumin) and the Reference sample provides 10% curcuminoid, 7:3 Ratio (GPGH & curcuminoid ratio 7:3) and 8:2 Ratio (GPGH & curcuminoid ratio 8:2).

TABLE 4

HPLC ANALYSIS

| | Component Amount (%) | | |
|---|---|---|---|
| Component | Reference Sample (10% Curcumin) | 7:3 Ratio | 8:2 Ratio |
| Bisdemethoxy Curcumin | 0.24299 | 0.2778 | 0.2713 |
| Demethoxy Curcumin | 0.74185 | 0.8160 | 0.8610 |
| Curcumin | 1.61957 | 1.6373 | 1.9358 |
| Total | 2.6044 | 2.7311 | 3.0681 |

Figure 5:
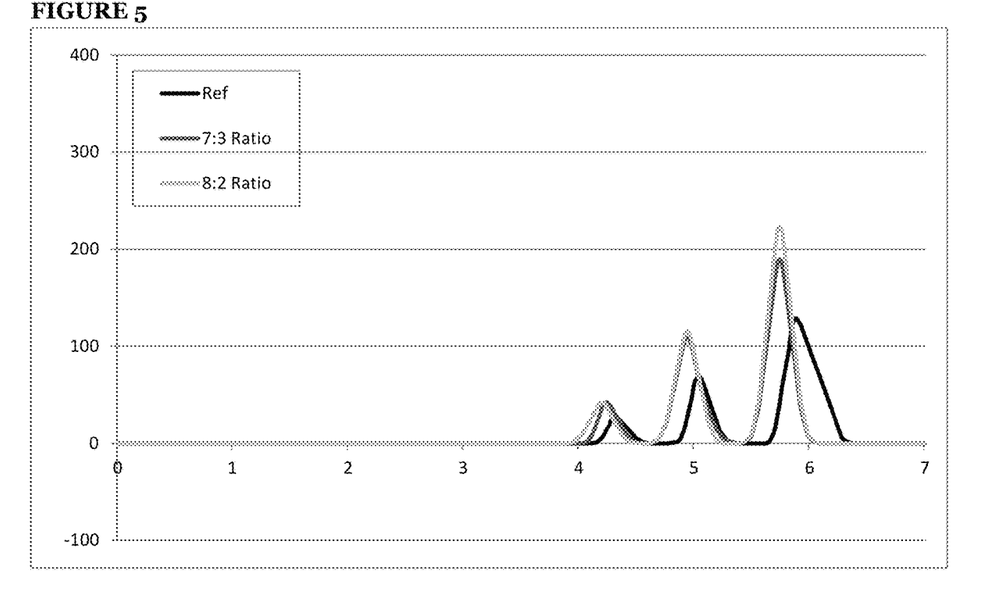
FIG. 5 shows a comparison of HPLC results for curcumin and compositions of steviol glycosides with GPGH.

FIG. 5 shows all three samples have similar HPLC chromatograms, although the Reference Sample (10% curcuminoid) is slightly shifted in retention time from the 7:3 and 8:2 compositions. This HPLC results show similar peaks for each component. It follows that the use of GPGH-curcuminoid mixtures has positive effects on curcumin solubility.

For this analysis, three different samples were prepared as follows: Reference Sample (Ref) 10% curcumin in MSM; 7:3 Ratio (GPGH & curcuminoid ratio 7:3); and 8:2 Ratio (GPGH & curcuminoid ratio 8:2 to demonstrate an optimal GPGH-to-curcuminoid ratio that provides exceptional water solubility of curcuminoids. HPLC analysis proceeded once the samples were prepared. As shown in TABLE 5 below, compares the water solubility of various compositions prepared with or without either water or ethanol and with various combinations of solubilization matrix (i.e. MSM, tyrosine, green tea extract, GPGH and steviol glycosides (STEVIA).

TABLE 5

SOLUBILITY WITH AND WITHOUT WATER OR ETHANOL

| Description | EtOH (g) | Water (g) | MSM (g) | Tyrosine (g) | Green Tea extract (g) | GPGH (g) | STEVIA (g) | Curcumin (g) | Water Solubility |
|---|---|---|---|---|---|---|---|---|---|
| MSM only (10% Curcumin) | | 8.1 | 0.9 | | | | | 0.1 | Grade 1 |
| MSM only (20% Curcumin) | | 7.2 | 0.8 | | | | | 0.2 | Grade 1 |
| MSM + STEVIA (8:2)/ water suspension | | 9 | 0.72 | | | | 0.18 | 0.1 | Grade 3 |
| MSM + STEVIA (7:3)/ water suspension | | 9 | 0.63 | | | | 0.27 | 0.1 | Grade 3 |

TABLE 5-continued

SOLUBILITY WITH AND WITHOUT WATER OR ETHANOL

| Description | EtOH (g) | Water (g) | MSM (g) | Tyrosine (g) | Green Tea extract (g) | GPGH (g) | STEVIA (g) | Curcumin (g) | Water Solubility |
|---|---|---|---|---|---|---|---|---|---|
| MSM + STEVIA (5:5) | | | 4.5 | | | | 4.5 | 1.0 | Grade 3 |
| MSM + STEVIA (8:2) | | | 7.2 | | | | 1.8 | 1.0 | Grade 4 |
| MSM + STEVIA (2:8) | | | 1.8 | | | | 7.2 | 1.0 | Grade 4 |
| MSM + STEVIA (7:3) | | | 6.3 | | | | 2.7 | 1.0 | Grade 4 |
| STEVIA Only | | 8.1 | | | | | 0.9 | 0.1 | Grade 4 |
| MSM + STEVIA (10% Curcumin) | | 7.2 | 0.9 | | | | 0.9 | 0.2 | Grade 4 |
| MSM + STEVIA (8:2)/ EtOH suspension | 9 | | 0.72 | | | | 0.18 | 0.1 | Grade 4 |
| MSM + STEVIA (7:3)/ EtOH suspension | 9 | | 0.63 | | | | 0.27 | 0.1 | Grade 4 |
| GPGH + STEVIA (8:2) | | | | | | 7.2 | 1.8 | 1 | Grade 4 |
| GPGH + STEVIA (7:3) | | | | | | 6.3 | 0.27 | 1 | Grade 4 |
| Tyrosine + STEVIA | | 7.2 | | 0.9 | | | 0.9 | 0.2 | Grade 4.5 |

\* Solubility Index 0 to 5: Grade 0 Not Soluble at all; Grade 1 Not soluble but changed color after stirring & vortex; Grade 2 Not soluble but changed color after stirring; Grade 3 Soluble but still showed precipitation and floating debris; Grade 4 without precipitation; and Grade 5 Good solubility regardless of amount of compound.
Where no water or EtOH is present, the curcumin is added to melted MSM and other solubility matrix component (for example, stevia), if present.

MSM was tested with EtOH, but the MSM sublimes easily due to its low melting point of about 109° C. Accordingly, it was very difficult to produce a powder with MSM and EtOH, since the MSM evaporates during the drying process along with the organic solvent. The formula of MSM+STEVIA (7:3)/EtOH suspension showed excellent solubility in water (Grade 4).

Figure 6:
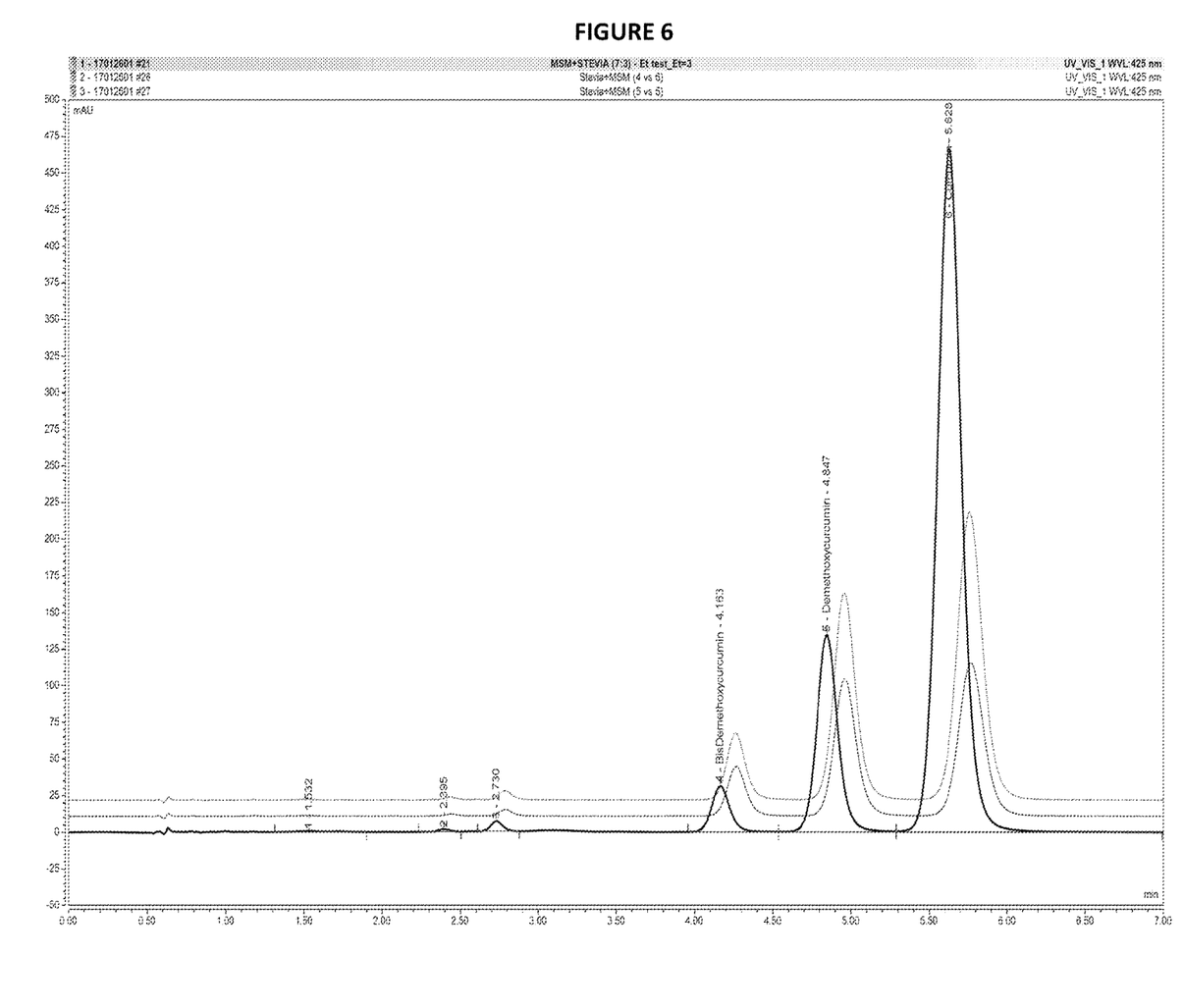
FIG. 6 shows a total amount of curcuminoid component for a curcuminoid composition comprising steviol glycosides with MSM from HPLC analysis in three MSM:steviol glycoside ratios (7:3; 6:4; and 5:5).

FIG. 6 shows different MSM-steviol glycosides ratios have similar effects on solubility of curcuminoids. However, as shown in TABLE 6 below, compositions with MSM-Steviol glycoside ratios of 7:3 and 5:5 have better solubility than the Reference sample (Theracurmin) that has no MSM-Steviol glycosides.

TABLE 6

SOLUBILITY COMPARISON OF "MSM + STEVIA" FORMULATIONS WITH DIFFERENT RATIOS

| | Component Amount (%) | | | |
|---|---|---|---|---|
| Component | Reference sample (Theracurmin) | MSM + Stevia (7:3) | MSM + Stevia (6:4) | MSM + Stevia (5:5) |
| Bisdemethoxy Curcumin | 0.24299 | 0.1699 | 0.1933 | 0.2594 |
| Demethoxy Curcumin | 0.74185 | 0.8512 | 0.6218 | 0.926 |
| Curcumin | 1.61957 | 3.4076 | 0.7965 | 1.4945 |
| Total | 2.60441 | 4.4287 | 1.6116 | 2.6799 |

Example 5: Analytical Method for Determining Curcumin in Plasma

Figure 1:
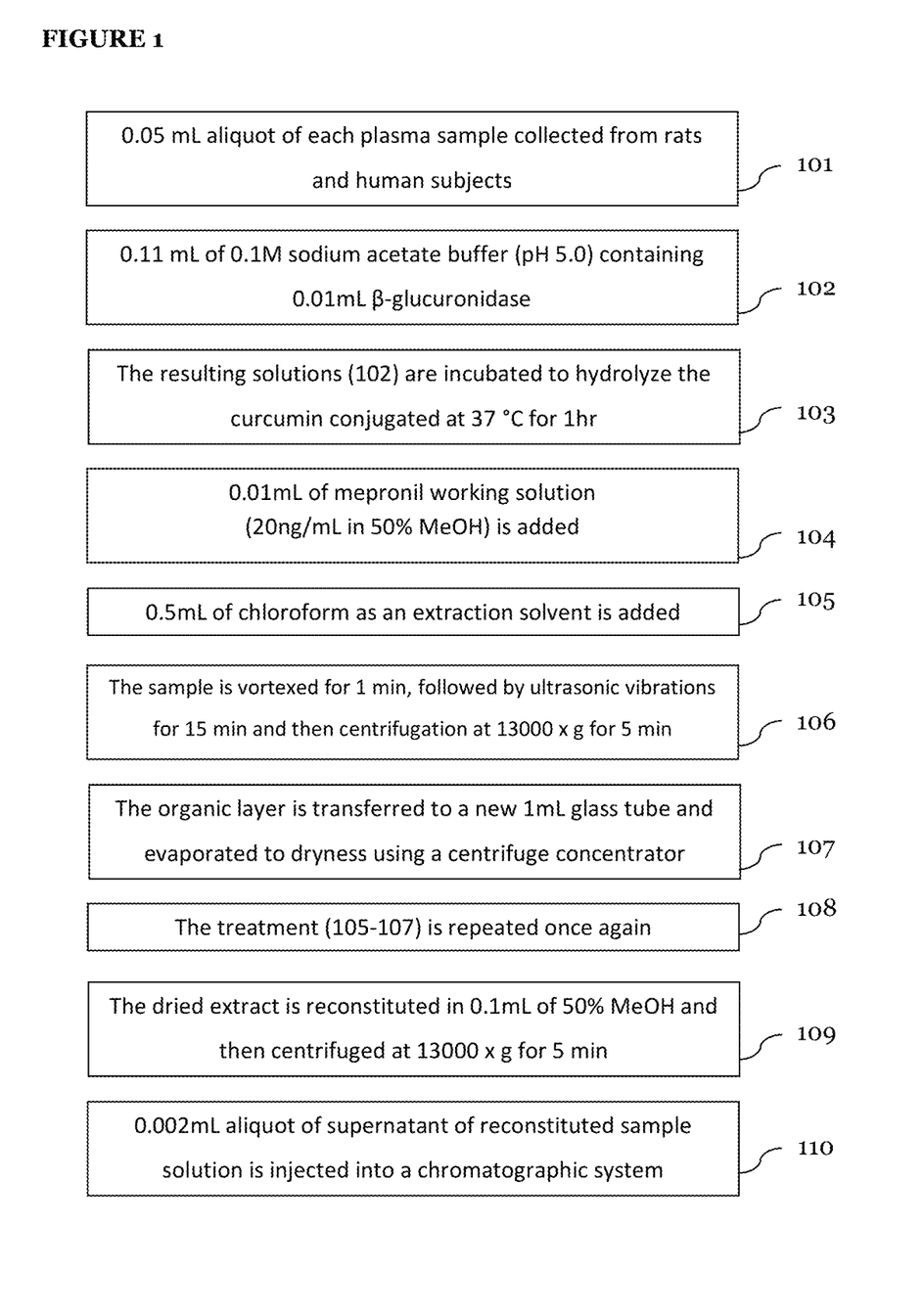
FIG. 1 shows a flow chart of the extracting process for plasma sample.

The present application also discloses an analytical method for determining curcumin in a subject's plasma sample (see FIG. 1) as set out below:

1. 0.05 mL aliquot of each plasma sample collected from a subject is transferred to a 1 mL glass tube (101);
2. 0.11 mL of 0.1 M sodium acetate buffer (pH 5.0) containing 0.01 mL β-glucuronidases added (102);
3. The resulting solutions (2) are incubated to hydrolyze the curcumin conjugated at 37° C. for 1 hr (103);
4. 0.01 mL of mepronil working solution (20 ng/mL in 50% MeOH) is added (104).
5. 0.5 mL of chloroform as an extraction solvent is added (105);
6. The sample is vortexed for 1 min, followed by ultrasonic vibrations for 15 min and then centrifugation at 13000×g for 5 min (106);
7. The organic layer is transferred to a new 1 mL glass tube and evaporated to dryness using a centrifuge concentrator (107);
8. The treatment (5-7) is repeated once again. (Add the organic layer to the same tube) (108);
9. The dried extract is reconstituted in 0.1 mL of 50% Methanol and then centrifuged at 13000×g for 5 min (109); and
10. 0.002 mL aliquot of supernatant of reconstituted sample solution is injected into an Liquid Chromatography—Mass Spectrometry system (110).

DISCUSSION

Both U.S. Pat. No. 8,551,507 and US20110033525 describe the use of stevioside and other steviol glycosides in conjunction with curcumin. However, both of the cited references first mix the compound with water, then with steviol glycosides. Such a process produces two problems: (1) since the target compound is water insoluble to begin with, its solubility will be limited by its particle-size prior to being mixed with water because water can never reach the center of the particles; and (2) the result is an aqueous composition that cannot be made into a solid dosage form. Whereas the methods described herein using a solubilization matrix overcomes both limitations.

Similarly, PCT/US2013/053585 also describes GPGH in conjunction with curcumin, but water is part of their compositions (i.e. aqueous) and used in the methods described.

Although various embodiments are described herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as any open-ended term, substantially equivalent to the phrase "including, but not limited to", and the words "comprise" and "comprises" have a corresponding meaning. As used herein, the singular forms "a", "an" and "the" include plural referents unless the context clearly dictates otherwise. Thus, for example, reference to "a thing" includes more than one such thing. The invention includes all embodiments and variations substantially as hereinbefore described and with reference to the examples and drawings.

Citation of references herein is not an admission that such references are prior art nor does it constitute any admission as to the contents or date of these documents.

What is claimed is:

1. A water soluble solid form powder composition, the powder composition consisting of:
   (a) a curcuminoid; and
   (b) a solubilizer, wherein the solubilizer is methylsulfonylmethane (MSM) and steviol glycoside in a ratio of 7:3 to 5:5.

2. The composition of claim 1, wherein the curcuminoid component of the solid form water soluble curcuminoid composition, is between about 5% and about 70% by weight;
   is between about 10% and about 60% by weight;
   is between about 10% and about 50% by weight;
   is between about 10% and about 40% by weight:
   is between about 10% and about 30% by weight: or
   is between about 10% and about 20% by weight.

3. The composition of claim 1, wherein the solubilizer is between about 30% and about 95% by weight;
   is between about 40% and about 80% by weight;
   is between about 40% and about 70% by weight;
   is between about 40% and about 60% by weight;
   is between about 50% and about 70% by weight; or
   is between about 70% and about 90% by weight of the solid form water soluble curcuminoid composition.

4. The composition of claim 1, wherein the solubilizer comprises an MSM and a steviol glycoside, and the MSM and the steviol glycoside together are between about 10% and about 90% by weight; or
   is between about 40% and about 80% by weight.

5. The composition of claim 1, wherein the solubilizer comprises MSM:steviol glycoside in a 7:3 ratio and together are between about 70% and about 90% by weight.

6. A solid dosage form, consisting of the water soluble solid form composition of claim 1, and a lubricant, a diluent, a gelatin, a modified cellulose, or a combination thereof, wherein the solid dosage form is in the form of a capsule, a tablet, or a pill.

* * * * *